(12) United States Patent
Wallace et al.

(10) Patent No.: US 10,338,065 B2
(45) Date of Patent: *Jul. 2, 2019

(54) DETECTION OF AMNIOTIC FLUID IN VAGINAL SECRETIONS OF PREGNANT WOMEN DUE TO PREMATURE RUPTURE OF FETAL MEMBRANES

(71) Applicant: Clinical Innovations, LLC

(72) Inventors: William Dean Wallace, Lehi, UT (US); Glen Ford, Montgomery Village, MD (US)

(73) Assignee: Clinical Innovations, LLC, Salt Lake City, UT (US)

( * ) Notice: Subject to any disclaimer, the term of this patent is extended or adjusted under 35 U.S.C. 154(b) by 601 days.

This patent is subject to a terminal disclaimer.

(21) Appl. No.: 14/120,800

(22) Filed: Jun. 30, 2014

(65) Prior Publication Data

US 2014/0315326 A1 Oct. 23, 2014

Related U.S. Application Data

(63) Continuation-in-part of application No. 12/923,099, filed on Sep. 1, 2010, now Pat. No. 8,765,487.

(51) Int. Cl.
*G01N 33/53* (2006.01)
*G01N 33/558* (2006.01)
*B01L 3/00* (2006.01)

(52) U.S. Cl.
CPC .......... *G01N 33/558* (2013.01); *B01L 3/5023* (2013.01); *G01N 2333/471* (2013.01); *G01N 2800/368* (2013.01)

(58) Field of Classification Search
CPC ....... G01N 2800/368; G01N 2333/471; G01N 33/525; G01N 33/558; B01L 3/5023
See application file for complete search history.

(56) References Cited

U.S. PATENT DOCUMENTS

| | | | |
|---|---|---|---|
| 4,803,998 A | 2/1989 | Kezes et al. | |
| 5,096,830 A | 3/1992 | Senyei et al. | |
| 5,554,504 A * | 9/1996 | Rutanen | G01N 33/689 435/7.8 |
| 5,597,700 A | 1/1997 | Konstantinov et al. | |
| 5,891,722 A | 4/1999 | Fuks et al. | |
| 7,232,253 B2 | 6/2007 | Isbitsky et al. | |
| 2002/0125273 A1 | 9/2002 | Sittler | |
| 2004/0266025 A1* | 12/2004 | Hickok | A61K 31/20 436/518 |
| 2008/0087624 A1 | 4/2008 | Buckley | |
| 2008/0188009 A1* | 8/2008 | Ford | G01N 33/558 436/518 |
| 2009/0038416 A1 | 2/2009 | Bonner | |

OTHER PUBLICATIONS

Kishida et al., (European Journal of Obstetrics and Gynecology and Reproductive Biology 1996; vol. 69, pp. 77-82).*
Guidelines for Reporting Statistics in Journals (J Neurophysiol92, (2004).*
Veress et al. (Magyar Noorvasol, 1992;vol. 55 issue 1,Abstract).*
Zegels G, Van Raemdonck GA, Tjalma WA, Van Ostade XW. Use of cervicovaginal fluid for the identification of biomarkers for pathologies of the female genital tract. Proteome Sci. Dec. 8, 2010;8:63.
Yamada H, Kishida T, Negishi H, Sagawa T, Yamaguchi M, Sato C, Nakamura I, Sato H, Sakai K, Yamaguchi T, Fujimoto S. Comparison of an improved AFP kit with the intra-amniotic PSP dye-injection method in equivocal cases of preterm premature rupture of the fetal membranes. J Obstet Gynaecol Res. Jun. 1997;23(3):307-11.
Shahin M, Raslan H. Comparative study of three amniotic fluid markers in premature rupture of membranes: prolactin, beta subunit of human chorionic gonadotropin, and alpha-fetoprotein. Gynecol Obstet Invest. 2007;63(4):195-9. Epub Dec. 7, 2006.
Rutanen E-M. Insulin-like growth factors in obstetrics. Curr Opin Obstet Gynecol (2000)12:163-168.
Rochelson BL, Rodke G, White R, Bracero L, Baker DA. A rapid colorimetric AFP monoclonal antibody test for the diagnosis of preterm rupture of the membranes. Obstet Gynecol. Feb. 1987;69(2):163-6.
Rochelson BL, Richardson DA, Macri JN. Rapid assay—possible application in the diagnosis of premature rupture of the membranes. Obstet Gynecol. Oct. 1983;62(4):414-8.
Neil PRL, Wallace EM. Is Amnisure useful in the management of women with prelabour rupture of the membranes? ANZJOG. 2010 50:534-538.
Lee SE, Park JS, Norwitz ER, Kim KW, Park HS, Jun JK. Measurement of placental alpha-microglobulin-1 in cervicovaginal discharge to diagnose rupture of membranes. Obstet Gynecol. Mar. 2007;109(3):634-40.
Lee MS, Lee J, Seong SH, et al. The clinical significance of a positive Amnisure test in women with term labor with intact membranes. J of Maternal-fetal and Neonatal Medicine. 2; 25(9): 1690-1698.
Kubota T and Takeuchi H. Evaluation of insulin-like growth factor binding protein-1 as a diagnostic tool for rupture of membranes. J Obstet Gynaecol (1998)18:33-36.
Guibourdenche J et al. Rapid detection of insulin-like growth factor-binding protein-1 and foetal fibronectin in cervico-vaginal secretions to diagnose premature membrane rupture. Ann Clin Niochem (1999)36:388-390.
Garite TJ, Gocke SE. Diagnosis of preterm rupture of membranes: is testing for alpha-fetoprotein better than ferning or nitrazine? Am J Perinatol. Jul. 1990;7(3):276-8.
Erdemoglu E and Mungan T. Significance of detection insulin-like growth factor binding protein-1 in cervicovaginal secretions: Comparison with nitrazine test and amniotic fluid assessment. Acta Obstet Gynecol Scand (2004) 83:622-626.

(Continued)

*Primary Examiner* — Julie Wu
*Assistant Examiner* — Carmencita M Belei
(74) *Attorney, Agent, or Firm* — TraskBritt

(57) ABSTRACT

A method is taught for the accurate determination of the premature rupture of membranes (PROM), defined as spontaneous rupture of membranes before the onset of uterine contractions. More specifically, a lateral flow assay strip tests for at least two antigens to greatly limit or eliminate the possibility of false negatives. A built-in timer in the cassette holding the lateral flow assay further increases the accuracy of the test. A collection buffer vial with self-contained shipping and dropper caps and built-in stand is also taught.

10 Claims, 3 Drawing Sheets

(56) References Cited

OTHER PUBLICATIONS

El-Messidi A, Cameron A. Diagnosis of Premature Rupture of Membranes:Inspiration From the Past and Insights for the Future. J.Obstet Gynaecol Can 2010;32(6):561-569, 2010.
Crandall BF, Hanson FW, Tennant F, Perdue ST. Alpha-fetoprotein levels in amniotic fluid between 11 and 15 weeks. Am J Obstet Gynecol. May 1989;160(5 Pt 1):1204-6.
Cousins LM, Smok DP, Lovett SM, Poeltler DM. AmniSurePlacental Alpha Microglobulin-1 Rapid Immunoassay versus Standard Diagnostic Methods for Detection of Rupture of Membranes. Am J Perinatol. Apr. 2005;22(6):317-320.
Cho, C.J., Shan, S.J., Winsor, E., Diamandis, E.P. Proteomic Analysis of Human Amniotic Fluid. Molecular & Cellular Proteomics. May 10, 2007. pp. 2-36.
Chen FC, Dudenhausen JW. Comparison of two rapid strip tests based on IGFBP-1 and PAMG-1 for the detection of amniotic fluid. Am J Perinatol. Apr. 2008;25(4)243-6.
Caughey, A., Robinson, J., Norwitz, E. Contemporary Diagnosis and Management of Preterm Premature Rupture of Membranes. Reviews in Obstetrics & Gnynecology. vol. 1 No. 1 2008, pp. 11-22.
Bennett SL, Cullen JB, Sherer DM, Woods JR Jr. The ferning and nitrazine tests of amniotic fluid between 12 and 41 weeks gestation. Am J Perinatol. Mar. 1993;10(2)101-4.

\* cited by examiner

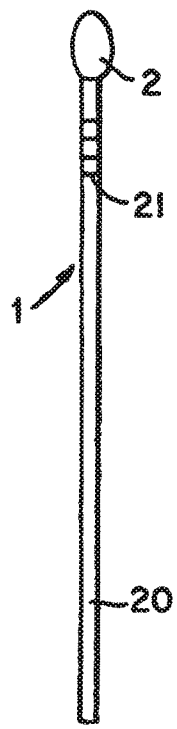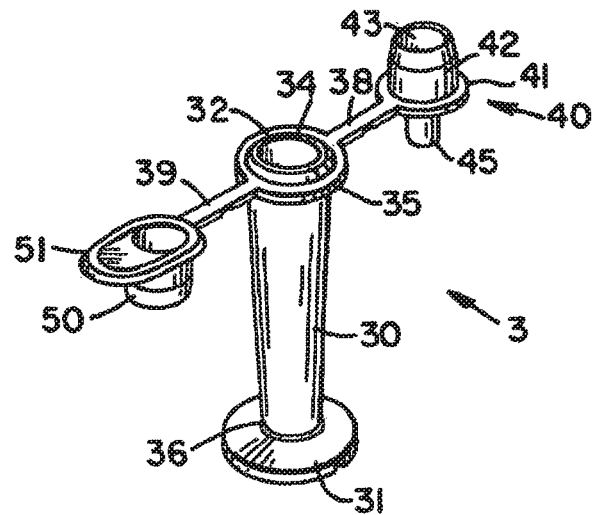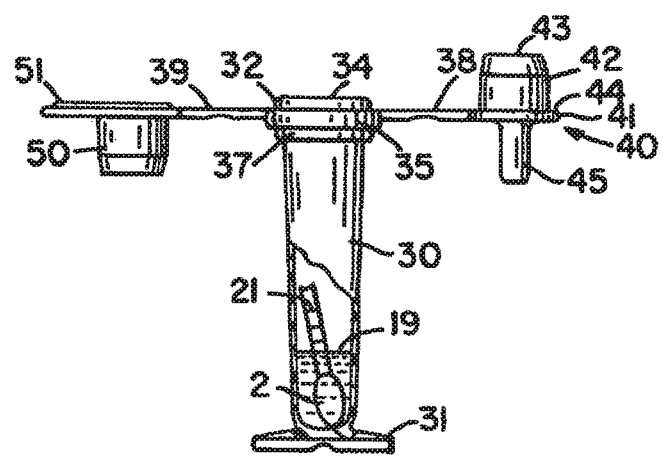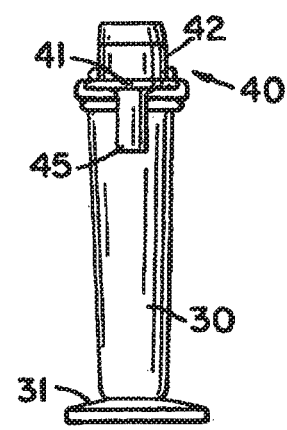
Fig.1
Fig.2
Fig.3
Fig.4

DETECTION OF AMNIOTIC FLUID IN VAGINAL SECRETIONS OF PREGNANT WOMEN DUE TO PREMATURE RUPTURE OF FETAL MEMBRANES

CROSS-REFERENCE TO RELATED APPLICATIONS

This application is a continuation in part of U.S. patent application Ser. No. 12/923,099, filed Sep. 1, 2010, now U.S. Pat. No. 8,765,487, issued Jul. 1, 2014, the disclosure of which is hereby incorporated herein in its entirety by this reference.

BACKGROUND

Premature rupture of membranes (PROM), defined as spontaneous rupture of fetal membranes before the onset of uterine contractions, is one of the most common diagnostic dilemmas in contemporary obstetric practice. PROM can occur at any gestational age, and preterm PROM (PPROM, defined as PROM before 37 weeks) is responsible for 20% to 40% of preterm births. This may result in infections, fetal distress and preterm birth, responsible for perinatal morbidity and mortality, strong damage or disorders for the fetus. The treatment of PROM depends not only on the stage of pregnancy and on the fetus maturity but also on the risk of infection and fetal distress. It is thus crucial to be able to diagnose PROM with accuracy at an early stage in order to decrease the risks of complications.

Early and accurate diagnosis of PROM would allow for gestational age-specific obstetric interventions designed to optimize perinatal outcome and minimize serious complications such as cord prolapse, preterm delivery, fetal distress and infectious morbidity (chorioamnionitis, neonatal sepsis). Conversely, a false-positive diagnosis of PROM may lead to unnecessary obstetric interventions, including hospitalization, administration of antibiotics and corticosteroids, and even induction of labor. Therefore, the correct and timely diagnosis of this disorder is of critical importance to the clinician because PROM and PPROM may be associated with serious maternal and neonatal consequences.

BRIEF SUMMARY

The disclosure uses a mixture of antibodies specifically reactive with two or more amniotic fluid proteins to detect a fetal membrane rupture. The antibodies are positioned on a lateral flow assay test strip. The use of this method reduces the level of false negatives from more than 10% to virtually zero.

In one embodiment of the disclosure, monoclonal and polyclonal antibodies specific for certain amniotic fluid proteins are used.

In one embodiment of the disclosure, a liquid sample is obtained by placing a long handled swab into the patient's vaginal vault. This sample is then placed into a buffer solution, contained within a vial.

After a swab has had enough time to release the markers into the buffer, the buffer sample is placed on the lateral flow assay in a specific site, such that the antigens are tagged by colorant tagged non-specific antibodies. The fluid sample then migrates by capillary action to the site of the monoclonal and polyclonal antibodies, wherein the antibodies specifically bind to the specific antigen present in the sample.

In one embodiment of the disclosure, the lateral flow assay test strip fits in, and is surrounded by a cassette.

In another embodiment of the disclosure, the lateral flow assay cassette contains a timer showing the elapsed time of the test as an integral part of the cassette.

The lateral flow assay test detects a combination of specific proteins present in amniotic fluid of pregnant women in all trimesters of pregnancy. These specific proteins are unique and found in much higher concentrations in amniotic fluid; therefore, they can be used as specific markers for the diagnosis for the rupture of fetal membranes.

In another embodiment of the disclosure, the present tests are easier to use, and less cumbersome, than prior tests.

In one embodiment of the disclosure, both the placental protein 12 (PP12) and betaIg-H3 biomarkers may be used to detect a fetal membrane rupture.

In another embodiment of the disclosure, fetal fibronectin may be used to detect fetal membrane rupture.

In another embodiment of the disclosure, alpha-fetoprotein (AFP) and prolactin may be used to detect fetal membrane rupture.

In one embodiment of the disclosure, the AFP and prolactin are tested in combination with PP12 to detect fetal membrane rupture.

In another embodiment of the disclosure, PP12 and AFP are used to detect fetal membrane rupture.

It should be noted that PP12 and AFP are believed to be more stable than most other suggested biomarkers and are found in higher concentrations in cervico-vaginal secretions than in maternal blood. Consequently, these two markers can be used in combination with each other, or with the other markers.

In another embodiment of the disclosure, creatinine and urea are used as markers, alone or in combination with other markers.

Another marker that may be used is Interleukin 6 (IL-6), alone or in combination with the markers listed above.

Specifically, monoclonal and polyclonal antibodies are strategically positioned at a test site on the lateral flow permeable test strip.

In a further embodiment, preeclampsia may be detected on the same lateral flow strip by using cystatin C, beta2-microglobulin, serum amyloid A, C-reactive protein (CRP), and neopterin.

This may be an argument that the combo PP12 combined with AFP is a better test for PROM, as they could be more stable over time than just the one alone. So in addition to the combo approach yielding a higher specificity for PROM (any of the molecules may be in higher concentration in the amniotic leaking fluid), one or another of them may be more stable and, therefore, more accurate results are obtained if the patient does not present to the doctor when she first starts leaking and then maybe stops leaking.

BRIEF DESCRIPTION OF THE DRAWINGS

The disclosure will be better understood and objects other than those set forth above will become apparent when consideration is given to the following detailed description thereof. Such description makes reference to the accompanying drawings wherein:

FIG. 1 is a perspective view of a swab;
FIG. 2 is a perspective view of a new vial;
FIG. 3 is a front view of the vial;
FIG. 4 is a side view of the vial.

DETAILED DESCRIPTION

Figure 5:
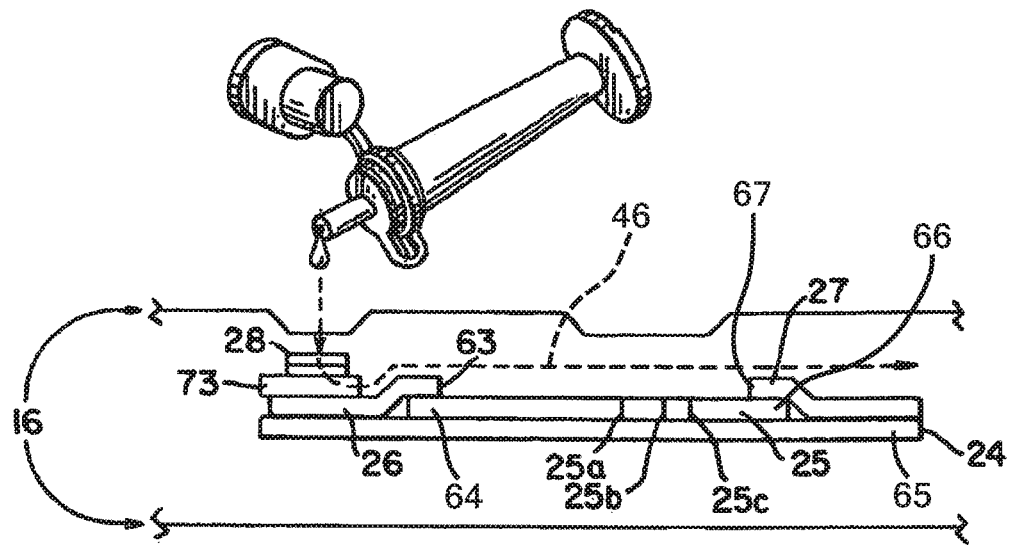
FIG. 5 is a side view of one embodiment of the lateral flow assay.

Referring to FIGS. 1-9, obtaining a fluid sample is the first step for the detection of PROM or PPROM. A sterile, long-handled swab 1 is removed from its packaging. A tip 2 of the swab should not touch anything prior to its insertion into the vaginal vault. The tip 2 is inserted two to three inches into the vaginal vault. After anywhere from about 15 seconds to about three minutes, the swab may be withdrawn.

The shipping cap of buffer vial 3 is opened, and the swab tip 2 is placed into the vial 3. The buffer in the vial may be a saline or phosphate buffer solution 19, or any other non-reactive buffer and preservatives (e.g., azide, proclin, thimerosal) as deemed necessary. While the vial that is used may be a standard vial, one embodiment of the vial 3 allows for a stand-alone vial that does not tip over. Specifically, the stand-alone vial 3 comprises a vial 30, with a bottom section 31 and a top section 32. The top section 32 has an opening 34 and a female collar 35 around the circumference of the opening 34. A stand 36 is attached to the bottom section 31 of the vial.

A male collar 37 snaps into the female collar. The male collar 37 comprises a first arm 38 and a second arm 39 positioned opposite to each other on the male collar 37.

A dropper 40 is positioned at and integral with a distal end 41 of the first arm 38. The dropper 40 comprises a stopper 42 having a hole 43 therein, the stopper 42 being positioned on a top side 44 of the distal end 41 of the first arm 38. A dispenser 45 is integral with the stopper. The dispenser 45 is positioned on the underside of the first arm 38. The stopper 42 is positioned so when the first arm 38 is bent, the stopper 42 fits snuggly in the opening of the vial, allowing for the dispensing of any liquid in the vial.

A cap 50 is positioned at and integral with a distal end 51 of the second arm 39, such that the cap fits snuggly into the opening 34 of the vial 3. The cap 50 at the distal end 51 of the second arm 39 can be positioned on the top side of the second arm 39. In another embodiment, the cap 50 can be positioned on the bottom side of the second arm 39 so that the arm is twisted to fit the cap 50 into the opening 34 of the vial 3.

After the swab tip 2 is placed in the buffer solution 19, a swab stick 20, which is scored 21, is broken off at a pre-scored location on the swab, and the vial is gently mixed for about 15 seconds to 1 minute, with the swab tip in the vial 3. Either before or after mixing the vial, the dropper 40 is fitted into the opening 34 of the vial 3. The solution may sit for about 15 seconds to five minutes, as needed.

A lateral flow assay strip positioned in a cassette is removed from a foil pouch, and about three to four drops of sample/buffer solution is added to the sample well of the cassette.

This lateral flow assay device, such as that used in Ser. No. 12/382,570, (filed Mar. 18, 2009, herein incorporated by reference) is used to test for PROM and PPROM by detecting the presence of the antigens in the buffer solution that were collected from the vaginal vault via the swab.

There are a variety of proteins or substances that can be tested on the lateral flow assay device, in a variety of combinations. Substances and proteins that can be tested include (PP12) and (BETA-Ig-H3), alpha-fetoprotein (AFP) prolactin, hCG, fetal fibronectin, etc., and combinations thereof. Embodiments may include at least two of the antigens listed, to ensure more accurate results. In one embodiment of the disclosure, both PP12 and alpha-fetoprotein (AFP) are tested.

The lateral flow assay device 22 being used for the detection of the antigens is comprised of a platform strip 24. It is preferred that the platform strip 24 be impermeable, and, preferably, laminated, and to that end, a plastic platform strip may be used. The platform strip 24 is elongated. Positioned on the top side of the platform strip 24 is a permeable membrane testing strip 25, where the mixture can bind or stick to the immobilized capture reagent, causing a color reaction, indicating the presence of the antigens. The presence and/or amount of analyte in the sample may be determined by the visibility of a line formed by the capture reagent 25a, specific for, in this case, PP12 and alpha-fetoprotein.

There may be more than one capture reagent and thus possibly more than one capture reagent site when a multiple of analytes are being tested and examined. There may also be a control reagent 25b, which is used to verify that the test is not giving any false positives or false negatives (depending on how the control is constructed). There may also be a second control region 25c so that there may be both a negative and a positive control. In addition, the control line could form a negative sign and the analytes or controls could form a positive line. The platform strip gives "body" and strength to the longitudinally positioned testing strip. A permeable membrane testing strip 25, which could be more properly called a "detection membrane strip 25," may be composed of a series of porous material pieces such as, paper, cotton, polyester, glass, nylon, mixed cellulose esters, spun polyethylene, polysulfones, and the like. Preferably, nitrocellulose, nylon or mixed cellulose esters are used for the analyte detection membrane testing strip 25. It can be attached to the platform strip by any number of means, including a variety of simple glues or tape, as long as the glues do not permeate up through and to the surface of the permeable membrane testing strip 25.

A sample receiving pad 26 to which the buffered sample is added is positioned on top of, and at a proximal end of, the non-permeable platform strip 24 while in contact with the permeable membrane testing strip 25. More specifically, a distal end 63 of the sample receiving pad 26 should either be in physical contact with a proximal end 64 of the permeable membrane testing strip 25 or the distal end 63 of the sample receiving pad 26 should be in contact with and overlap the proximal end 64 of the sample receiving pad 26. The sample receiving pad 26 may be composed of a series of porous material pieces such as, paper, cotton, polyester, glass, nylon, mixed cellulose esters, spun polyethylene, polysulfones, and the like. Paper, cotton, polyester, glass fiber, and/or polyethylene are generally used for the sample receiving pad. A conjugate pad 28 positioned above or below, or even next to the sample pad allows for the tagging of the sample.

The conjugate pad 28 itself is comprised of paper, cotton, polyester, glass fiber, or polyethylene. More importantly than the material of the conjugate pad are the lyophilized colorants in the pad. The dried or lyophilized conjugate in the conjugate pad 28 may consist of latex microparticles, enzymatic, fluorescent, or visually observable tags. These other tags include metal sols, enzymatic, fluorescent, latex microparticles, and the like, preferably colloidal gold particles. The conjugate is to provide a means of identifying any reaction or binding at the site of the capture reagent 25a. These means can include visual, fluorescence, radioactive, etc. The colorant is attached to a non-specific mouse monoclonal antibody that binds to an epitope of the antigens in the sample.

Additionally, the monoclonal antibodies to the antigens being tested may be attached to the gold, latex, selenium, carbon or other metallic colloids that are used as the colorant. By having a monoclonal antibody attached to the colorant, there is a greater enhancement of the results on the test strip as the colorant, with the monoclonal antibody bound to the specific ligand, migrates to the testing site. Specificity is enhanced, as well as the color at the detection site.

The conjugate pad 28 may be positioned on top or below the sample receiving pad 26.

In another embodiment a semi-permeable membrane 73 resides directly on top of the sample receiving pad 26, and the conjugate pad 28 resides on top of the semi-permeable membrane 73. The semi-permeable membrane 73 serves as a temporary obstruction that breaks down when the combined effects of the sample volume and surface tension cause the sample to eventually run through semi-permeable membrane laminating membrane 24. Hatched fibers may be used in semi-permeable membrane 73 creating micropores. The extended time for the mixing of the analyte and the conjugate results in greater analyte detection sensitivity. The semi-permeable membrane is constructed of micropores of diameters between 0.01 micron and 20 microns, allowing the sample to slowly diffuse through the semi-permeable membrane. The semi-permeable membrane may also be constructed of hydrophobic material or hatched fibers creating micropores, thus allowing for the slow diffusion of sample mixed with conjugate through the semi-permeable membrane. Different semi-permeable membranes with different size ranges can be used, depending on the biological sample for which the assay is being performed. For instance, one could have a semi-permeable membrane having a preferred pore size range of about 10 microns to about 20 microns. In other instances, the sizing of the membrane can be used to screen for certain ligands or other materials. For the present disclosure, a semi-permeable membrane having a pore size range of about 8 nm to about 20 nm is used to test for proteins.

As the now conjugated sample on the platform strip 24 migrates into the flow membrane, the analyte-particle conjugate is carried along flow path 46 where resolved on the membrane coated with analyte reactive substances. In a positive result, the conjugate-analyte complex reacts with the capture antibodies attached to the analyte detection membrane of the permeable membrane testing strip 25 at the site of the capture reagent 25a.

The analytes at the detection site include polyclonal anti-human PP12 antibodies and monoclonal and polyclonal anti-human alpha-fetoprotein antibodies. The detection site may also contain monoclonal antibodies, which were mixed with the polyclonal antibodies prior to being dried or lyophilized onto the test strip membrane. The combination of the alpha-fetoprotein and the PP12 has an increased signal due to the combining of the signals from the target molecules contained in the microgram/nanogram range in the amniotic fluid. Generally, the ratio of polyclonal antibodies blended together are 75% PP12 to 25% alpha-fetoprotein antibodies. In addition, it is known (Shahin et al.) that AFP rises during the first and second trimester and decreases during the third trimester, while PP12 continues to rise during the third trimester, this making the combination for detection for the presence of amniotic fluid in cervicovaginal fluid more sensitive throughout pregnancy.

In another embodiment, polyclonal anti-human antibodies may be positioned at the site of the colorants, to allow for an increase in the chemical complex at the reaction site.

As noted above, a variety of different antibodies may be used in different combinations to test for PROM. In the case of beta-Ig-H3, there is some evidence that the antigen is found in small amounts in serum. Thus, a dilution series may be set up to dilute the vaginal swab sample for testing. As the sample is diluted, only the presence of beta-Ig-H3 in the vaginal sample will be detected.

The monoclonal anti-human PP12 antibodies being used (obtained from R & D Systems) were produced from a hybridoma resulting from the fusion of a mouse myeloma with B cells obtained from a mouse immunized with purified *E. coli*-derived recombinant human insulin-like growth factor binding protein 1 (rhPP12). The IgG fraction of the ascites fluid was purified by Protein G affinity chromatography. PP12 is one of several proteins that bind IGF with high affinity and modulate IGF activity. PP12 binds equally well to IF-I and IGF-11. PP12 is expressed in liver, decidua, kidneys and is the most abundant in amniotic fluid. The antibody is lyophilized from a 0.2 µm filtered solution in phosphate-buffered saline (PBS) with 5% trehalose. PBS is also used to reconstitute the antibody. If reconstituted with 1 mL of PBS, the antibody concentration will be 500 µg/mL.

Polyclonal anti-human PP12 antibodies can be used. More specifically, the use of Human PP12 Affinity Purified Polyclonal antibodies can vastly reduce the number of false negatives often found in other tests, due to the attachment or attraction to the number of different epitopes is greatly increased. Put another way, the polyclonal antibodies bind to multiple epitopes. This allows for a greater chance of capturing the majority of PP12 molecules as they transverse the membrane. The antibody is produced in goats or sheep immunized with purified *E. coli*-derived, recombinant human insulin-like growth factor binding protein 1 (rhPP12). PP12 specific IgG was purified by human PP12 affinity chromatography. Going through the same lyophilization process as the monoclonal antibody, reconstitution of the lyophilized polyclonal antibody yields an antibody concentration of 0.1 mg/ml.

The lateral flow assay test may also test for alpha-fetoprotein. Both monoclonal anti-human alpha-fetoprotein antibody and polyclonal anti-human alpha-fetoprotein antibody are used. It should be noted that a number of different monoclonal anti-human PP12 antibodies and anti-human alpha-fetoprotein antibodies are used, wherein the antibodies are specific for different specific epitopes. This further allows for an increase in the accuracy of the test.

In one embodiment of the disclosure, the ratio of the PP12 antibodies to AFP antibodies ranges from about 5:1 to about 10:1. This applies to either the monoclonal antibodies for PP12 and AFP or the polyclonal antibodies for PP12 and AFP, or a mixture of the antibodies for either PP12 or AFP.

Other monoclonal and polyclonal antibodies may be used with respect to other antigens that may be used on the test strip for the termination of PROM. The monoclonal and polyclonal antibodies may be used in the arrangements described above, and manufactured as described or by other manufacturing techniques used to make monoclonal or polyclonal antibodies.

The polyclonal antibodies positioned specific for both the alpha-fetoprotein and the antibodies specific for the PP12 may be mixed, or kept in separate lines. A blend could comprise a first set of monoclonal antibodies for the detection of the first biomarker indicating the premature rupture of fetal membranes; and a second set of monoclonal antibodies for the detection of the second biomarker, the second biomarker being indicative of the premature rupture of fetal membranes. The first set of polyclonal antibodies and the second set of polyclonal antibodies can be intermingled with the first set of monoclonal antibodies. The second set of monoclonal antibodies can next be intermingled with the others. In either version of the test, the antibodies in the capture site may be in a straight line, circle, "+" sign, or any other design that will be distinctive and easy to recognize. Similarly, any and all monoclonal antibodies that may be positioned at the capture reagent site are positioned in a similar fashion.

A control site 25b is positioned following the capture reagent 25a site. The control reagent site gives a positive result in the form of a line, circle, etc., in the presence of the colorant tagged antibodies. If there is no positive line, the test is faulty, and needs to be repeated. Rabbit anti-mouse antibodies are used at the control site.

In another embodiment, either before or following a control line 100, or even without the presence of a control line 100, which comprises anti-PP12 antibodies for the detection of the presence of PP12. These antibodies of control line 100 are polyclonal antibodies, monoclonal antibodies, or both. A positive result, meaning that a visible line appears, or that some other human or machine signal appears, indicates the presence of PP12 in the tested fluid, serves as evidence of a rupture of the fetal membrane.

In another embodiment, either before or following a control line 100, or even without the presence of a control line 100, and with or without the presence of the PP12 line, there is a test line 110 for the detection of fragmented PP12. The test line 110 comprises monoclonal antibodies and/or polyclonal antibodies specific for fragmented PP12. A positive result, meaning that a visible line appears, or that some other human or machine signal appears along the line, indicates that there is the presence of fractured PP12 in the tested fluid. The presence of fragmented PP12 can be evidence of fetal distress, most likely due to rupture of the fetal membrane, and/or fetal infection or inflammation as evidence of potential pre-term birth.

In yet another embodiment, another line 120, with or without the presence of the other lines mentioned above (except for the main test line), tests for the presence of proteases. In one embodiment, the protease is a Mortella protease (MMP-8). The test line 120 comprises anti-MMP-8 antibodies and, in this case, dual monoclonal antibodies. In another embodiment, polyclonal antibodies or a mixture of polyclonal and monoclonal antibodies are used. A positive result, meaning that a visible line appears, or that some other human or machine signal appears along the line, indicates that there is the presence of the protease(s) in the tested fluid. The presence of protease(s) can be evidence of fetal distress, most likely fetal infection/inflammation as evidence of potential pre-term birth.

It should be noted that variations of the basic lateral flow device described above, such as a change in the position of the semi-permeable membrane, may unexpectedly greatly improve the accuracy of the lateral flow assay, and allows for crisp clear reaction lines that allow for easy visual or machine readability.

The reaction lines can be visualized and the results displayed and/or recorded by a cell phone. The cell phone has an app programmed with an algorithm, to read the results, based on the intensity of the lines. The cell phone can then display the results, translating the signals on the assay into human decipherable images, letters, and numbers. In one embodiment, the results on the lateral flow assay are read by the cell phone just as a bar code would be read and translated.

Figure 6:
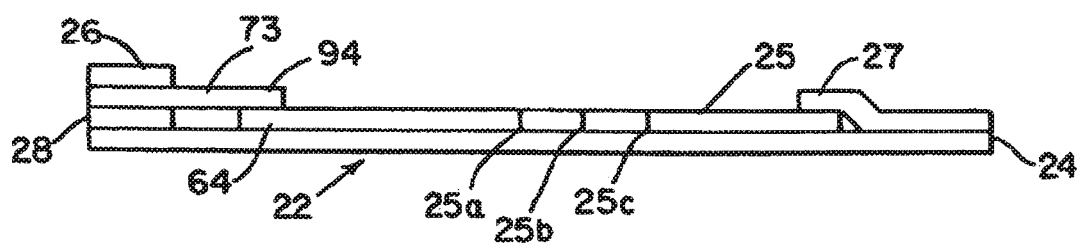
FIG. 6 is a side view of another embodiment of the lateral flow assay.
Figure 7:
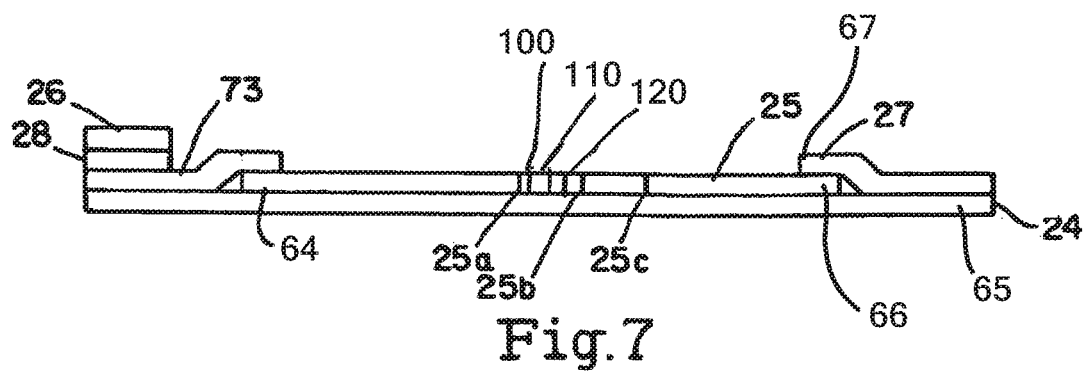
FIG. 7 is a side view of yet another embodiment of the lateral flow assay.
Figure 8A:
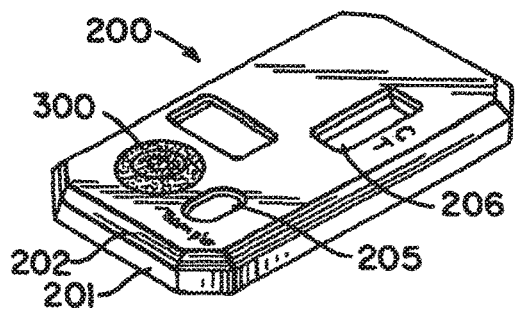
FIG. 8A is a perspective view of a cassette.
Figure 8B:
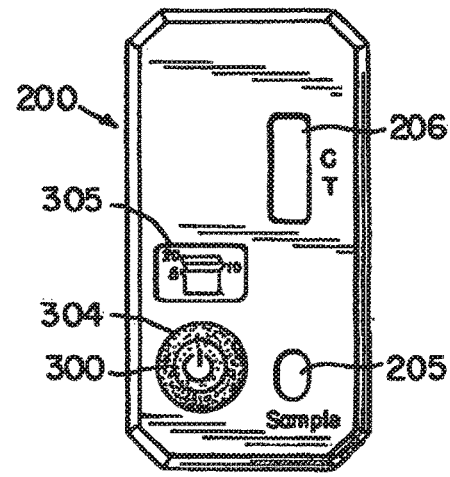
FIG. 8B is a top view of the cassette.
Figure 9:
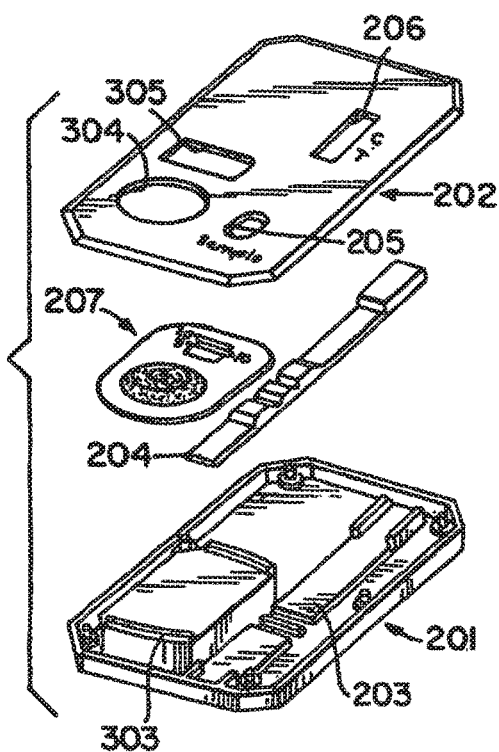
FIG. 9 is an exploded view of the cassette.
Figure 10:
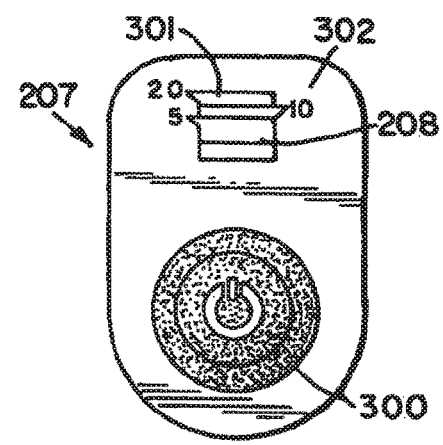
FIG. 10 is a perspective view of the timing device.

In one embodiment, and as shown in FIG. 6, the semi-permeable membrane 73 is positioned on top of and in contact with the old conjugate pad 28, and underneath and in contact with the sample receiving pad 26. A distal end 94 of the semi-permeable membrane 73 overlaps onto, or, more precisely, on top of the proximal end 64 of the permeable membrane testing strip 25. In this circumstance, it is preferred that the semi-permeable membrane 73 be in contact with and preferably overlapping the permeable membrane testing strip 25 at proximal end 64. The conjugate pad 28 and the permeable membrane testing strip 25 are not in contact with each other.

The semi-permeable membrane 73 serves a couple of different purposes when positioned over the gold conjugate pad 28 and underneath the sample receiving pad 26. First, particulate matter and ligands not being tested can be trapped by the semi-permeable membrane 73, dependent, of course, on the pore size of the semi-permeable membrane 73. This in and of itself greatly improves results, as the problem of non-specific binding is eliminated. Second, the rate of the flow of the sample is decreased, thereby preventing the diluent or supernatant from washing over the conjugate pad 28, thereby producing inconclusive or inaccurate results. Third, and as noted above, the semi-permeable membrane 73 is restrictive, and slows down the flow of the conjugate sample, thereby increasing the amount of time the conjugate reacts with the ligand or analyte, giving clearer, more defined, results. By reducing the speed of the flow of the sample, thereby resulting in the sample and conjugate label being in contact for a longer amount of time before flowing along the semipermeable membrane, allows more time for ligands and gold conjugates to continue to bond.

It should also be noted that the flow of fluid along the lateral flow assay is reduced, which also aids in the reading of the results. The detection site of the capture reagent 25a is not overwhelmed by a volume of fluid that may inadvertently washout some of the antibody or other detection means at the site of the capture reagent 25a.

In another embodiment of the disclosure (FIG. 7), the semi-permeable membrane 73 is positioned under and in contact with the conjugate pad 28, which, in turn, is positioned under and in contact with the sample receiving pad 26. In this embodiment, the distal end of the semi-permeable membrane 73 is again in contact with and overlapping the permeable membrane testing strip 25 of the lateral flow assay. As described above, neither the conjugate pad nor the sample pad are in contact with the permeable membrane testing strip 25. Only the semi-permeable membrane 73 is in contact with and on top of the permeable membrane testing strip.

The length of the sections of the semi-permeable membrane and the sample receiving pad overlapping the permeable membrane testing strip is normally no more than about 5-8 millimeters. This distance can be varied depending upon the experiments run, and the preference of the user, if so desired.

While it is generally preferred that gold conjugate particles be used, other metal sol conjugates may also be used.

As an alternative to using metals (generally attached to antibodies), antibodies attached to a dye with an extinction coefficient equal to or greater than gold may be used. (The metal sol particles or dyes should have a high extinction coefficient equal to or greater than gold.) There are a large number of other visible conjugates that may be used for the attachment of the tag to a ligand. Indeed, in some circumstances, the conjugate need not be visible to the naked eye, but must be detectable by some means such as UV light, other light frequencies, readable by machine, etc.

The solid phase particles useful in connection with the disclosure may comprise, for example, particles of latex or of other support materials such as silica, agarose, glass, polyacrylamides, polymethyl methacrylates, carboxylate modified latex and Sepharose. Preferably, the particles will vary in size from about 0.02 micron to about 10 microns. In particular, useful commercially available materials include 0.99 micron carboxylate modified latex, cyanogen bromide activated Sepharose beads (Sigma), fused silica particles (Ciba Corning, lot #6), isothiocyanate glass (Sigma), Reactogel 25DF (Pierce) and Polybead-carboxylate monodisperse microspheres. In accordance with the disclosure, such particles may be coated with a layer of FAB, intact antibody, proteins, peptides, lipids, and the like, coupled thereto in a manner known per se in the art to present the solid phase component.

Additionally, in another component of the lateral flow assay, a reservoir absorbent pad 27 is positioned on top of and at a distal end 65 of the non-permeable membrane platform strip 24 while in contact with the distal end 66 of the permeable membrane testing strip 25. It is preferred that the proximal end 67 of the reservoir absorbent pad 27 overlaps the distal end 66 of the permeable membrane testing strip 25, while the distal end of the reservoir absorbent pad 27 is attached to the distal end 65 of the non-permeable membrane platform strip 24. The reservoir absorbent pad 27 helps draw the fluid sample across the permeable membrane testing strip 25 by capillary action. The reservoir absorbent pad 27 may be composed of a series of porous material pieces such as, paper, cotton, polyester, glass, nylon, mixed cellulose esters, spun polyethylene, polysulfones, and the like. Preferably, the reservoir absorbent pad 27 is comprised of paper, cotton, polyester, glass fiber, or polyethylene.

In one embodiment of the disclosure, the assay strip is in a cassette 200. The cassette is a case that encompasses a bottom section 201 and a top section 202. The bottom section contains a seat 203 into which a lateral strip 204 fits. The top section 202 contains a sample well (opening) 205 under which is positioned the sample site of the lateral flow assay strip.

Three or four drops of the sample/buffer are added to the sample well 205 of the cassette 200. After an appropriate amount of time, the results of the test are visible through a test window 206. Normally, it is advisable to wait 5-10 minutes for test results to manifest. Strong leakage of amniotic fluid (higher analyte concentrations) may make the results visible early (within 1-3 minutes) while a small leak make take a full 10 minutes. The test is valid even if the stripes are faint or uneven.

To assist in determining the passage of time once the sample/buffer has been added to the sample well, a capillary flow timer 207 is included in the cassette 200. While electronic or analog timers could be used, the present disclosure includes a capillary flow timer 207 based on the movement of a fluid by capillary action. The capillary flow timer 207 being used (created by Timestrip Technical Services Ltd., U.S. Pat. No. 7,232,253, herein incorporated by reference) can be designed to run from about five minutes to about twenty minutes, with an accuracy of ±10% in time under isothermal conditions. By pressing button 300, a seal (not shown) is broken, and fluid 208 flows, by capillary action (not shown), to an enclosed cavity 301 for which there are markings 302 indicating the amount of time that has passed since the button 300 was pressed at the time of the application of the sample.

The capillary flow timer 207 fits on a raised surface 303 on the bottom section 201 of the cassette. The top section 202 includes a window 304 for the button 300 and a second timer window 305 to view the elapsed time.

Once the sample is added, and the button is pressed, the user of the assay kit can periodically check to see how much time has elapsed in order to get an accurate reading of the results and to determine, in part, the seriousness of the PPROM. At that point, the OB/GYN can make a determination as to the method of treatment.

The entire disclosure of each document cited (including patents, patent applications, journal articles, abstracts, laboratory manuals, books, or other disclosures) in the specification is hereby incorporated herein by reference.

While the disclosure has been described in conjunction with specific embodiments, it is evident that many alternatives, modifications and variations will be apparent to those skilled in the art in light of the foregoing description. Accordingly, the present disclosure attempts to embrace all such alternatives, modifications and variations that fall within the spirit and scope of the appended claims.

What we claim is:

1. A method for the detection of biomarkers in vaginal secretions of pregnant women indicative of premature rupture of fetal membranes, the method comprising:
    a) obtaining a fluid sample by placing a sterile swab in a vaginal vault of a pregnant woman;
    b) removing the swab from the vaginal vault after a period of time from about fifteen seconds to about three minutes, and placing the swab in a vial containing a buffer solution;
    c) allowing time for the fluids from the swab to be released into the buffer solution;
    d) adding a few drops of the buffer solution that has been exposed to the fluids from the swab to a chromatographic specific binding assay strip device, the device created by including the following components:
        i) a non-permeable platform strip;
        ii) a permeable membrane testing strip positioned on top of the non-permeable platform strip, the permeable membrane testing strip further comprising a test site for the detection of the premature rupture of fetal membranes, the site comprising a blend, the blend comprising at least:
            1) a first set of polyclonal antibodies for the detection of a first biomarker, the first biomarker indicating the premature rupture of fetal membranes, the first biomarker being alpha-fetoprotein;
            2) a second set of polyclonal antibodies for the detection of a second biomarker, the second biomarker being indicative of the premature rupture of fetal membranes, the second biomarker being placental protein 12;
            3) a first set of monoclonal antibodies for the detection of the first biomarker being indicative of the premature rupture of fetal membranes, the first set of monoclonal antibodies being specific for alpha-fetoprotein; and 4) a second set of monoclonal antibodies for the detection of a second biomarker, the second biomarker being indicative of the premature rupture of fetal membrane the second set of monoclonal antibodies being specific for placental protein 12;
wherein the ratio of polyclonal antibodies blended together are about 75% placental protein 12 to about 25% alpha-fetoprotein antibodies;
iii) a sample receiving pad positioned on top of and at a proximal end of the non-permeable platform strip while in contact with a proximal end of the permeable membrane testing strip;
iv) a reservoir pad positioned on top of and at a distal end of the non-permeable membrane testing strip while in contact with a distal end of the permeable membrane test strip; and
v) a conjugate pad positioned on top of or below the sample receiving pad, the conjugate pad comprising a permeable membrane containing a conjugate, the conjugate comprising a colorant attached to antibodies that can attach to analytes in the sample, wherein the conjugate of the sample binds to the analytes forming conjugate tagged analytes;
e) allowing time for the conjugate tagged analytes to migrate along the length of the permeable membrane strip to the test site; and
f) detecting binding between the biomarkers and their respective the monoclonal antibodies and the polyclonal antibodies by the presence of an indicator line at the test site.

2. The method according to claim 1, wherein the first set of monoclonal antibodies and the second set of monoclonal antibodies are fixed to the colorant on the conjugate pad.

3. The method according to claim 2, wherein the first set of polyclonal antibodies and the second set of polyclonal antibodies are positioned at the test site in the shape of a plus sign.

4. The method according to claim 1, wherein the first set of polyclonal antibodies and the second set of polyclonal antibodies are intermingled with the first set of monoclonal antibodies and the second set of monoclonal antibodies.

5. The method according to claim 4, wherein the first set of polyclonal antibodies and the second set of polyclonal antibodies intermingled with the first set of monoclonal antibodies and the second set of monoclonal antibodies are positioned at the test site in the shape of a plus sign.

6. The method according to claim 1, further comprising the detection of additional biomarkers, the additional biomarkers selected from the group consisting of: BETA-IG-H3, prolactin, hCG, and fetal fibronectin.

7. The method according to claim 6, wherein the alpha-fetoprotein biomarkers and prolactin biomarkers are tested in combination with the placental protein 12 biomarker to detect the fetal membrane rupture.

8. The method according to claim 1, wherein the chromatographic specific binding assay strip device further comprises a semi-permeable membrane, wherein the semi-permeable membrane is positioned between the sample receiving pad, and the conjugate pad residing on top of the semi-permeable membrane.

9. The method according to claim 1, wherein the chromatographic specific binding assay strip device further comprises a semi-permeable membrane, wherein the semi-permeable membrane is positioned over the conjugate pad, the conjugate pad being positioned over the sample receiving pad.

10. A method for detecting biomarkers in vaginal secretions, the method comprising:
a) obtaining a fluid sample by placing a sterile swab in a vaginal vault of a pregnant woman;
b) removing the swab from the vaginal vault after a period of time from about fifteen seconds to about three minutes;
c) afterwards placing the swab in a vial containing a buffer solution;
d) allowing time for fluid from the swab to release into the buffer solution in the vial;
e) adding buffer solution that has been contacted with the swab to a chromatographic specific binding assay strip device comprising:
i) a non-permeable platform strip;
ii) a permeable membrane testing strip positioned on top of the non-permeable platform strip, the permeable membrane testing strip comprising a test site for detecting the premature rupture of fetal membranes, the test site comprising a blend, wherein the blend comprises at least:
1) a first set of polyclonal antibodies for detecting alpha-fetoprotein;
2) a second set of polyclonal antibodies for detecting placental protein 12;
3) a first set of monoclonal antibodies specific for detecting alpha-fetoprotein; and
4) a second set of monoclonal antibodies specific for detecting placental protein 12;
wherein the ratio of polyclonal antibodies blended together are about 75% placental protein 12 to about 25% alpha-fetoprotein antibodies;
iii) a sample receiving pad positioned on top of and at a proximal end of the non-permeable platform strip while in contact with a proximal end of the permeable membrane testing strip;
iv) a reservoir pad positioned on top of and at a distal end of the non-permeable membrane testing strip while in contact with a distal end of the permeable membrane test strip; and
v) a conjugate pad positioned on top of or below the sample receiving pad, the conjugate pad comprising a permeable membrane containing a conjugate, the conjugate comprising a colorant attached to antibodies that bind with analytes in the sample, wherein the conjugate of the sample binds to the analytes to form conjugate tagged analytes;
f) allowing time for conjugate tagged analytes to migrate along the length of the permeable membrane strip to the test site; and
g) detecting binding between alpha-fetoprotein, placental protein 12, and their respective monoclonal and polyclonal antibodies at the test site.

* * * * *